United States Patent [19]

van Dijk

[11] Patent Number: 4,568,346

[45] Date of Patent: Feb. 4, 1986

[54] HYPODERMIC SYRINGE HAVING A TELESCOPIC ASSEMBLY BETWEEN CARTRIDGE AND MEDICAMENT HOLDER

[75] Inventor: Jan van Dijk, Olst, Netherlands

[73] Assignee: Duphar International Research, B.V., Weesp, Netherlands

[21] Appl. No.: 544,853

[22] Filed: Oct. 24, 1983

[30] Foreign Application Priority Data

Oct. 27, 1982 [NL] Netherlands ......................... 8204141

[51] Int. Cl.⁴ ............................................... A61B 19/00

[52] U.S. Cl. ...................................... 604/414; 604/88; 604/234

[58] Field of Search ................... 604/86, 88, 198, 200, 604/201, 225, 232, 234, 235, 244, 283, 414, 415

[56] References Cited

U.S. PATENT DOCUMENTS

| | | | |
|---|---|---|---|
| 336,924 | 8/1967 | Sarnoff et al. | 604/415 |
| 4,328,802 | 5/1982 | Curley et al. | 604/88 |
| 4,449,539 | 5/1984 | Sarstedt | 128/764 |

*Primary Examiner*—C. Fred Rosenbaum
*Assistant Examiner*—Karen Kaechele
*Attorney, Agent, or Firm*—Stevens, Davis, Miller & Mosher

[57] ABSTRACT

The invention relates to a hypodermic syringe comprising a cartridge having connected thereto an injection needle, a medicament holder closed by means of a piercible stopper, and a telescopic assembly which detachably connects the cartridge and the holder. The part of the injection needle extending within the telescopic assembly is surrounded entirely by a sheath of a flexible material the closed end of which bears against or is present at a short distance from the stopper of the medicament holder.

16 Claims, 4 Drawing Figures

HYPODERMIC SYRINGE HAVING A TELESCOPIC ASSEMBLY BETWEEN CARTRIDGE AND MEDICAMENT HOLDER

The invention relates to a hypodermic syringe comprising a cartridge having an injection needle connected thereto, a medicament holder closed by means of a piercible stopper, and a telescopic assembly which connects the cartridge and the holder so as to be detachable. The telescopic assembly comprises an outer telescopic member which is connected to the medicament holder and an inner telescopic member which is movable within said outer telescopic member and one end of which is detachably connected to the cartridge. The injection needle extends within the telescopic assembly so that, as a result of an inwardly telescopic movement of the telescopic members relative to each other, the needle pierces the stopper and connects the interior of the cartridge with that of the medicament holder. In this manner the liquid present in the cartridge can reach the medicament in the medicament holder and dissolve it, after which the resulting injection liquid can be drawn into the cartridge. The cartridge with injection needle can then be detached from the telescopic assembly and is then ready for administering an injection.

Such a hypodermic syringe is disclosed in Netherlands patent application No. 7412096 in the name of Applicants.

However, some disadvantages have been established in assembling this already known hypodermic syringe. During said assembly, the injection needle provided on the cartridge is inserted into the telescopic assembly until the inner telescopic member adjoins the needle holder, with which the needle is connected to the cartridge, in a sterile and sealing manner. The risk that during said assembly step the sterility of the needle may be lost, is not excluded. Moreover, damage to the needle tip frequently occurs because during this step the tip of the needle can contact the inner wall of the narrow inner telescopic member. These disadvantages occur even more easily because the above-described assembly step is hardly suitable for automation, because the access for the needle is narrow and the needle is not always accurately centered. Therefore, said assembly step must usually be carried out manually.

In the above-mentioned Netherlands patent application No. 7412096, provisions are described which better ensure the sterility of the needle during storage and transport of the hypodermic syringe. The improvement which is achieved by means of these provisions is remarkable indeed, but in practice it has been found that nevertheless the inner telescopic member prematurely works loose from the needle holder in a small number of cases, as a result of which the sterility of the needle may be lost. In order to prevent this, a sterile sealing sheath around the part of the injection needle extending in the telescopic assembly would be highly desirable.

Such a needle guard manufactured from form-retaining material, for example polypropylene, is known for a one-chamber syringe, for example from Netherlands patent application No. 7401607 in the name of Applicants. When such a rigid sheath is used as a needle guard, however, it must first be removed before the needle can be pierced through the stopper so as to place the interior of the cartridge in communication with that of the medicament holder. Herewith the sterility of the needle can easily be lost. Moreover, when the needle connected to the cartridge is placed into the telescopic assembly again, the risk is present that the tip of the needle may be damaged. In addition, use of this type of needle guard requires a few extra operations to make the syringe ready for use, while pre-filled hypodermic syringes are meant to facilitate and expedite the administration of an injection.

Netherlands patent application No. 6505766 relates to a mixing syringe comprising a vial, a syringe and telescoping members for detachably connecting the vial with the syringe container. FIGS. 8-10 show a modification of this known syringe, wherein the needle end is covered by a rigid sleeve. Said sleeve is integrally connected with the end of the inner telescopic member by a frangible portion. When telescoping the members the covering sleeve fractures and is shifted backwards, the needle piercing the rigid sleeve. This known construction has several drawbacks. A narrowed rigid sleeve extending from the inner telescopic member and connected therewith by a frangible portion is difficult to produce by moulding and vulnerable during assemblage. The tolerances in the dimensions of the moulded parts are very small. During assembly the needle tip or the rigid sleeve can easily be damaged, in the latter case the sterility of the needle being compromised. Last but not least, it is almost impossible to use this known syringe without damaging or blunting the needle tip when piercing the rigid wall of the covering sleeve.

It is the object of the present invention to avoid the disadvantages which may occur during the assembly of the hypodermic syringe, namely the possibility of damage or loss of sterility of the injection needle, without losing the advantages of the hypodermic syringe described in the above-mentioned Netherlands patent application No. 7412096.

This object can be achieved by means of a hypodermic syringe of the kind mentioned in the opening paragraph which is characterized in that the part of the injection needle extending in the telescopic assembly is surrounded entirely by a sheath of a flexible material, preferably rubber of a quality which is acceptable for pharmaceutical applications. It has been found that when such a protective sheath of a flexible material is used, the needle easily pierces both the closed end of the sheath and the stopper when the telescopic members are moved inwardly with respect to each other, provided the closed end of the sheath bears against or is present at a short distance from the stopper of the medicament holder. During the inserting movement of the telescopic members relative to each other, the closed end of the protective sheath is retained by the stopper, as a result of which the protective sheath is compressed so that the needle successively pierces the closed end of the sheath and the stopper.

It has been found that the force which is necessary to insert the telescopic members inwardly with respect to each other is only slightly greater when a sheath according to the invention is used than without a protective sheath. As a result of this fact, the user does not need to apply hardly any extra force to make the hypodermic syringe ready for administering an injection.

It may occur that the needle tip during piercing of the rubber sheath is deflected and comes into contact with the neck of the medicament holder or is jammed in the rubber collar of the stopper extending within said neck. As a result of this, damage to the tip of the needle may occur or the desired open communication with the medicament holder may not be produced, respectively.

In order to avoid these potential problems it has proved advantageous to provide the outer telescopic member with centering means for the sheath which surround the sheath laterally in the proximity of its closed end. Said centering means preferably comprise at least three rib-like elements which extend inwardly radially from the inner wall of the outer telescopic member. Said rib-like elements usually form an integrated part of the outer telescopic member and are manufactured from form-retaining material, for example a synthetic resin. Such an outer telescopic member of synthetic resin provided with rib-like elements can be manufactured by means of injection moulding.

After producing the open communication between cartridge and medicament holder, the liquid present in the cartridge is injected into the medicament holder so as to dissolve the medicament. The resulting injection liquid is then drawn into the cartridge through the needle. In order to enable the administration of an injection, the cartridge with injection needle is then detached from the telescopic member. As stated above, it is of importance that any extra operation which is necessary to make a prefilled syringe ready for use, should be avoided. Therefore, the flexible sheath should preferably be removed from the needle simultaneously with the detaching of the cartridge with injection needle from the telescopic assembly. This has provded possible indeed in that, according to another aspect of the present invention, the inner telescopic member is provided internally with a circumferential, whether a not interrupted, ridge or cam. As a result of this provision, during detachment of the cartridge with injection needle from the inner telescopic member, the sheath remains in the telescopic assembly.

To prevent unintended telescoping of the assembly, a safety member may be present outside between the telescopic members, e.g. in the form of a clip.

BRIEF DESCRIPTION OF THE DRAWINGS

The present invention will now be described in greater detail with reference to the accompanying drawings, in which.

Figure 1:
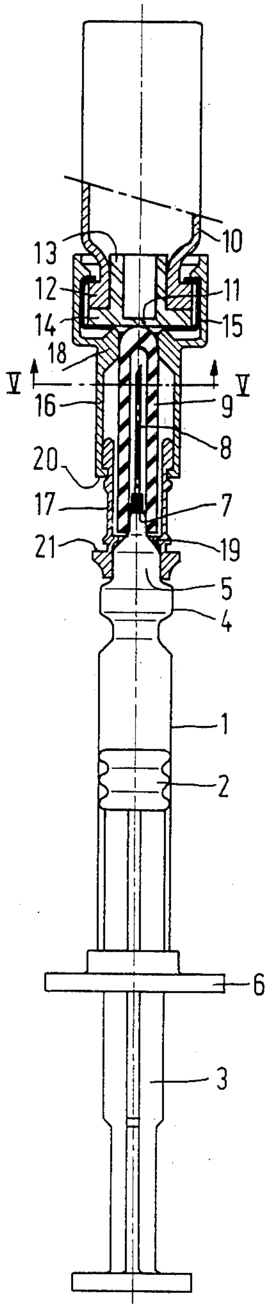
FIG. 1 is a longitudinal sectional view of a hypodermic syringe according to the invention in the condition in which it is transported and stored.

Reference numeral 1 in FIG. 1 denotes a cartridge which at one end has a finger grip 6 and at the other end has a neck with a flange around which the collar 4 of an aluminium needle holder 5 is riveted. A piston 2 having a piston rod 3 is present in the cartridge. An injection needle 8 is connected in a sealing manner in a sleeve-like narrowed portion 7 of the needle holder, while inside the needle holder a membrane, not shown in the drawing, may be present to keep the liquid in the cartridge separated from the sharp rear end of the needle, as shown in the above-mentioned Netherlands patent application No. 7412096. The injection needle is surrounded by a protective sheath 9 of rubber of a pharmaceutical quality, the open end of which is slid in a sealing manner around the sleeve 7 of the needle holder, and the closed end of which engages the stopper of the medicament holder.

The medicament holder 10 comprises a stopper having a piercible central portion 11, a collar 13 extending in the neck 12 of the medicament holder and a flange 14. The stopper is connected to the medicament holder by means of a riveted capsule 15 having a central aperture.

Cartridge and medicament holder are connected together by means of a telescopic assembly consisting of an outer telescopic member 16 and an inner telescopic member 17. The outer telescopic member is clamped around the neck of the medicament holder, the inner member is detachably connected (clamped) to the needle holder with a thickened end portion 21. The outer telescopic member is provided internally with three centering ribs 18 for the protective sheath, the inner telescopic member is provided with a circumferential ridge 19. Between the end 20 of the outer telescopic member and the thickened end portion 21 of the inner member a safety clip can be provided, to prevent unintended telescoping of the members with respect to each other. In outline, the telescopic assembly is further constructed as described and shown in the above-mentioned Netherlands patent application No. 7412096.

Figure 4:
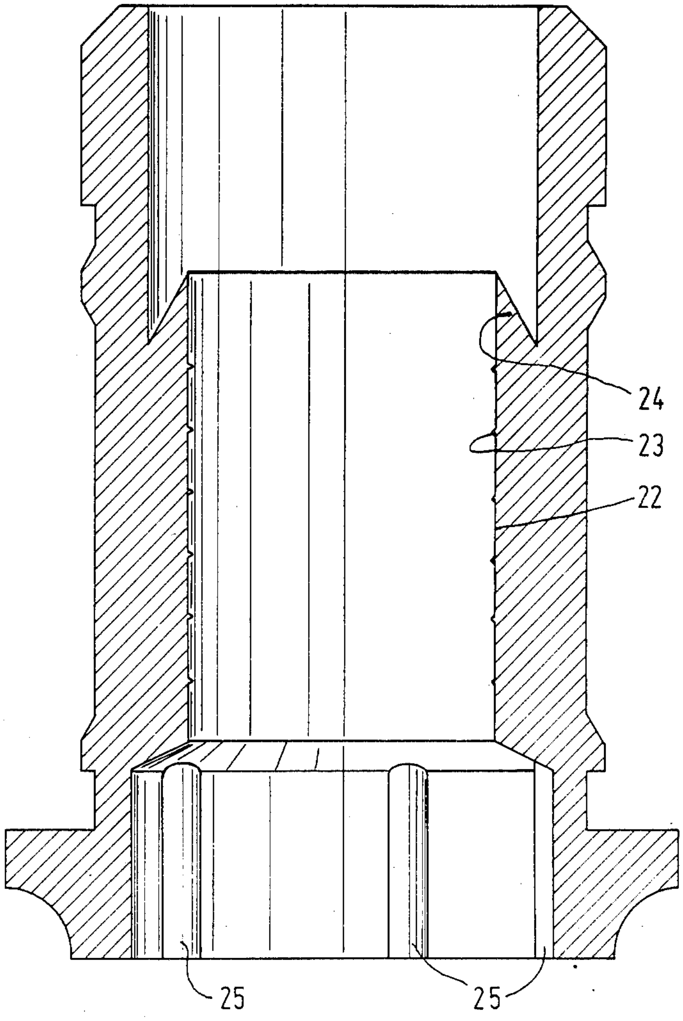
FIG. 4 shows a different and preferred embodiment of the inner telescopic member to be used in the syringe of the invention.
Figure 5:
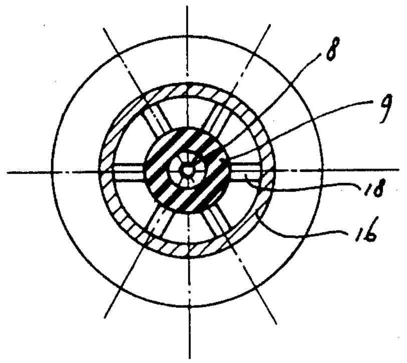
Figure 6:
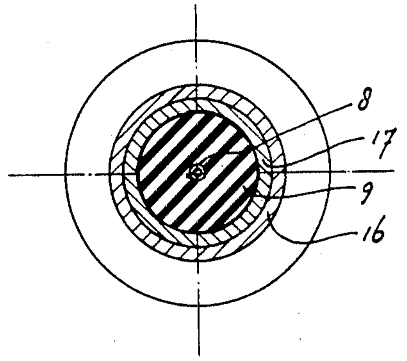

In a different and preferred embodiment of the syringe of the present invention, the inner telescopic member is designed as shown in FIG. 4. Said inner member presents a narrowed inward portion with a rough inner surface 22. Said rough surface is obtained by providing the inner wall with a number of small circumferential ridges 23. Said narrowed inward portion terminates upwards into a circumferential cam 24, with a sharp angle obliquely protruding upwards, i.e. in the direction of the connection with the outer telescopic member. In another equally preferred embodiment said cam is interrupted, forming a number of teeth obliguely protruding upwards. The above embodiments have proven to be preferably suited for retaining the flexible needle sheath within the telescopic assembly when the cartridge with injection needle is detached from the inner telescopic member. The neck portion of the inner telescopic member is provided on the inner wall with five longitudinal ribs 25 for a tight connection to the needle holder sleeve, allowing small tolerances in the dimensions of said sleeve.

The hypodermic syringe according to the invention may be assembled as follows; said assembly takes place for the greater part in a sterile room:

The cartridge comprising a piston is filled on its front with a solvent for the medicament. The collar of the needle holder in which a needle surrounded by a flexible sheath in a sterile manner is already connected, is then slid around the flange on the front of the filled cartridge, after which the collar is riveted around the flange. During the above-described assembly step a membrane may be clamped between the needle holder sleeve and the flange, if so desired. The above operations are carried out in the sterile room, after which assembling may be finished outside said room. The outer telescopic member of the telescopic assembly is now clamped around the neck of the medicament holder containing the medicine. The cartridge comprising needle and protective sheath is then inserted into the inner telescopic member until the inner telescopic member is connected in a clamping manner around the needle holder sleeve. The finger grip and the piston rod may be mounted at any desired moment during the assembly process; this may also take place outside the sterile room.

The syringe is now ready for transport and storage after having been packaged.

Figure 2:
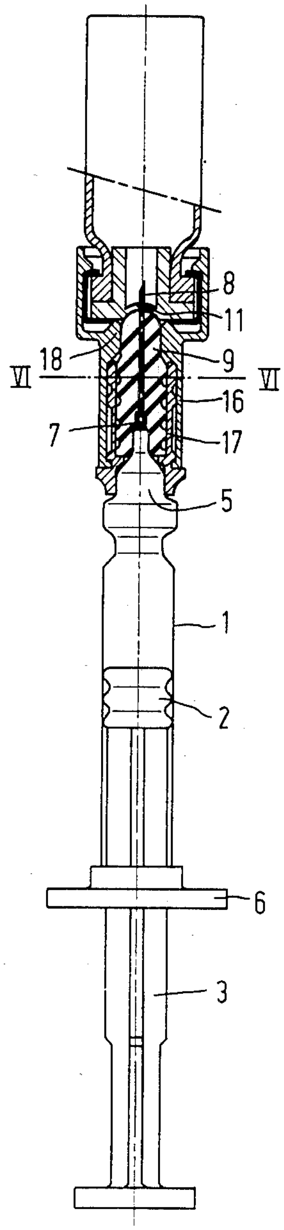
FIG. 2 is a longitudinal sectional view of the same syringe as shown in FIG. 1, but this time after the open communication between cartridge and medicament holder has been produced.

When the hypodermic syringe according to the invention is used, first, of course after the safety clip, if present, has been removed, the telescopic members are telescoped by exerting an inwardly directed force on the cartridge relative to the medicament holder. The injection needle pierces both the closed end of the protective sheath and the central portion of the stopper so that an open communication is produced between the interior of the cartridge and that of the medicament holder. During said inwardly telescoping movement, the flexible sheath is compressed between the needle holder and the stopper. The needle pierces the closed end of the sheath approximately centrally due to the centering ribs 18 in the outer telescopic member. The position then reached is shown in FIG. 2.

Figure 3:
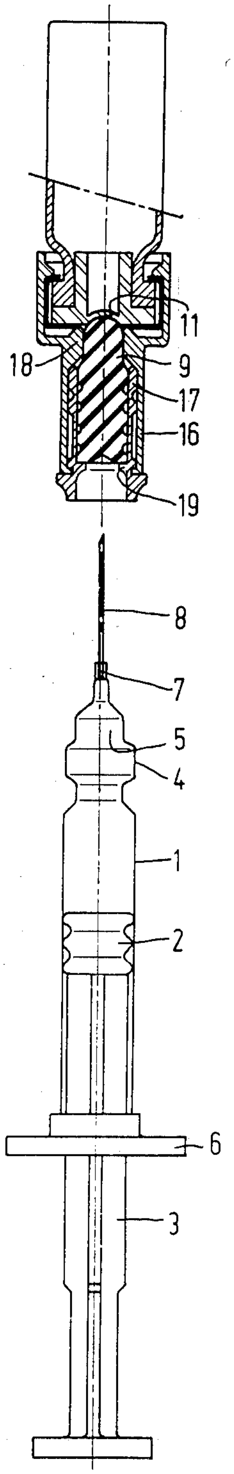
FIG. 3 shows again the same syringe as in FIGS. 1 and 2, but this time after the cartridge with needle has been detached from the telescopic assembly.

The solvent in the cartridge is then injected into the medicament holder after which, for example with slight swinging or shaking, the contents of the medicament holder are dissolved in the liquid. The resulting injection liquid is then again drawn into the cartridge. This can best be done by holding the syringe with the medicament holder (obliquely) upwards. When the injection liquid has been drawn into the cartridge as completely as possible, a force directed away from the cartridge is exerted on the telescopic assembly. As a result of this force, the inner telescopic member detaches from the needle holder, while simultaneously the protective sheath remains behind the circumferential ridge 19 (or the cam 24 respectively) in the inner telescopic member and is removed from the needle in this manner. The position then reached is shown in FIG. 3.

An injection may then be administered by means of the syringe.

I claim:

1. A hypodermic syringe comprising a cartridge having an injection needle connected at a narrowed portion thereof;

a medicament holder closed by means of a pierceable stopper; and a telescopic assembly detachably connecting the cartridge and the holder, said telescopic assembly comprising an outer telescopic member that is connected to the medicament holder and an inner telescopic member that is movable within said outer telescopic member and is detachably connected to the cartridge;

said injection needle surrounded entirely by a sheath of flexible material, said sheath having an open end and a closed end, said open end of said sheath engaging said narrow portion of said syringe wherein said closed end is centered by contact with said outer telescoping member;

both of said injection needle and sheath extend within the telescopic assembly so that, as a result of an inward telescopic movement of the telescopic members relative to each other, the sheath is compressed into sealing engagement between said needle and said inner and outer telescopic members, the needle pierces the sheath and the stopper and connects the interior of the cartridge with that of the medicament holder.

2. A hypodermic syringe as claimed in claim 1, wherein the outer telescopic member further comprises centering means for the sheath that laterally surround the sheath in the proximity of its closed end.

3. A hypodermic syringe as claimed in claim 2, wherein the centering means comprises at least three rib-shaped elements that extend radially inwardly from an inner wall of the outer telescopic member.

4. A hypodermic syringe as claimed in claim 2, wherein the inner telescopic member further comprises at least one ridge that extends radially inwardly from an inner wall of said member, said ridge retaining the sheath within the telescopic assembly when the cartridge is detached from the inner telescopic member and the injection needle is removed from the assembly.

5. A hypodermic syring as claimed in claim 3, wherein the inner telescopic member further comprises at least one ridge that extends radially inwardly from an inner wall of said member, said ridge retaining the sheath within the telescopic assembly when the cartridge is detached from the inner telescopic member and the injection needle is removed from the assembly.

6. A hypodermic syringe as claimed in claim 4, wherein the outer telescopic member further comprises inwardly directed means to lock said inner and outer telescopic members together upon completion of the inwardly telescopic movement of said telescopic members.

7. A hypodermic syringe as claimed in claim 5, wherein the outer telescopic member further comprises inwardly directed means to lock said inner and outer telescopic members together upon completion of the inwardly telescopic movement of said telescopic members.

8. A hypodermic syringe as claimed in claim 1, wherein said closed end of said sheath bears against or is present a short distance from the stopper of the medicament holder prior to telescoping said inner and outer telescopic members.

9. A hypodermic syringe comprising a cartridge having an injection needle connected at a narrowed portion thereof;

a medicament holder closed by means of a pierceable stopper; and a telescopic assembly detachably connecting the cartridge and the holder, said telescopic assembly comprising an outer telescopic member that is connected to the medicament holder and an inner telescopic member movable within said outer telescopic member and is detachably connected to the cartridge, said inner telescopic member further comprising at least one ridge that extends radially inwardly from an inner wall of said member;

said injection needle surrounded entirely by a sheath of flexible material, said sheath having an open end and a closed end, said open end of said sheath engaging said narrowed portion of said syringe;

wherein said closed end is centered by contact with said outer telescoping member both of said injection needle and sheath extend within the telescopic assembly so that, as a result of inwardly telescopic movement of the telescopic members relative to each other, the sheath is compressed into sealing engagement between said needle and said inner and outer telescopic members, the needle pierces the sheath and the stopper and connects the interior of the cartridge with that of the medicament holder;

said ridge on said inner telescopic member retaining the sheath within the telescopic assembly when the cartridge is detached from the inner telescopic member and the injection needle removed from the assembly.

10. A hypodermic syringe as claimed in claim 9, wherein the inner telescopic member includes a narrowed inward portion having a first end adjacent the cartridge and a second end remote from the cartridge, the second end of said portion terminating to form a plurality of teeth that protrude upwardly toward the outer telescopic member at an oblique angle, said portion retaining the flexible sheath within the telescopic assembly when the cartridge is detached from the inner telescopic assembly.

11. A hypodermic syringe as claimed in claim 10, wherein the narrowed inward portion includes a plurality of inwardly extending circumferential ridges.

12. A hypodermic syringe as claimed in claim 9, wherein the closed end of said sheath bears against or is present a short distance from the stopper of the medicament holder prior to telescoping said inner and outer telescopic assemblies.

13. A hypodermic syringe as claimed in claim 9, wherein the outer telescopic member further comprises centering means for the sheath that laterally surround the sheath in the proximity of its closed end.

14. A hypodermic syringe as claimed in claim 13, wherein the centering means comprises at least three rib-shaped elements that extend radially inwardly from an inner wall of the outer telescopic member.

15. A hypodermic syringe as claimed in claim 9, wherein the inner telescopic member includes a narrowed inward portion having a first end adjacent the cartridge and a second end remote from the cartridge, the second end of said portion terminating to form a circumferential cam that protrudes upwardly toward the outer telescopic member at an oblique angle, said portion retaining the flexible sheath within the telescopic assembly when the cartridge is detached from the inner telescopic assembly.

16. A hypodermic syringe as claimed in claim 15, wherein the narrowed inward portion includes a plurality of inwardly extending circumferential ridges.

* * * * *